US005487899A

United States Patent [19]
Davis

[11] Patent Number: 5,487,899
[45] Date of Patent: Jan. 30, 1996

[54] WOUND HEALING

[75] Inventor: Robert H. Davis, King of Prussia, Pa.

[73] Assignee: Jess Clarke & Sons, Inc., Westport, Conn.

[21] Appl. No.: 190,330

[22] Filed: Jan. 31, 1994

[51] Int. Cl.$^6$ .................................................. A61K 9/70
[52] U.S. Cl. ............................... 424/443; 424/195.1
[58] Field of Search .......................... 424/195.1, 447

[56] References Cited

U.S. PATENT DOCUMENTS 4,242,120  12/1980  Mannankov ........................ 71/89
4,959,214   9/1990  McAnalley ...................... 424/195.1
5,188,655   2/1993  Jones et al. ......................... 71/92 X
5,266,318  11/1993  Taylor-McCord .............. 424/195.1
5,322,689   6/1994  Hughes et al. ..................... 424/401

*Primary Examiner*—Gollamudi S. Kishore
*Assistant Examiner*—Sharon Howard
*Attorney, Agent, or Firm*—Yahwak & Associates

[57] ABSTRACT

The present invention describes a composition derived from the Aloe plant which when used as an adjuvant for the healing of wounds exhibits increased anti-inflammatory and wound healing activity. The composition, an Aloe vera mucilage at approximately a 1:1 ratio, preferably with Aloe pulp fibers, increased open wound healing activity and increased wound tensile strength by 131% over controls.

8 Claims, 5 Drawing Sheets

EFFECT OF DILUTION ON THE VISCOSITY OF ALOE VERA AND MUCILAGE (1:1 RATIO)

WOUND HEALING

The ability of an organism to activate the wound healing process effectively and promptly is essential for its survival. When a wound is created, blood vessel integrity is violated, causing leakage of platelets and other blood products into surrounding tissues resulting in local inflammation. Platelets function to initiate homeostasis and they activate other substances such as chemotactic factors involved in further homeostasis and production of cell-migratory factors. There are constituents of blood called intrinsic factors that regulate the homeostatic mechanism so as to prevent total homeostasis. These homeostatic mechanisms result in local inflammation.

In the inflammatory phase there are two major cell types which can be found in the wound fluid: neutrophils and monocytes. Both cell types are attracted to the wound site by chemotactic factors that are released immediately upon blood vessel disruption. Early in the inflammatory phase, neutrophils are the first cells seen at the wound site and are primarily responsible for scavenging bacterial and foreign material. Late in the inflammatory phase, monocytes migrate to the site, and once there they undergo a phenotypic transformation into a macrophage. These macrophages have dual roles: to scavenge any remaining bacterial and to release growth factors which stimulate granulation tissue formation.

Granulation tissue formation consists of new blood vessel formation (angiogenesis), fibroblast activity (fibroplasia), and re-epithelialization. Endothelial cells and fibroblasts are attracted to the wound site by means of growth factors and chemotactic factors released from macrophages. As these two cell types proliferate, they undergo transformation which allows for the sprouting of new capillary buds, and the cell motility as well as the deposition of extracellular matrix consisting of loosely organized collagen, fibronectin, and hyaluronic acid. Once the extracellular matrix is in place, cells begin to adhere to each other, as well as to the extra-cellular matrix. As this occurs, tension is generated across the wound and will cause contraction.

Re-epithelialization occurs when there is a suitable granular bed for epithelial cells to move across. Upon injury, epithelial cells at the wound edge lose contact inhibition and undergo a transformation allowing them to migrate and proliferate in a manner such that one cell overrides the next. Once the defect has been mended, tissue integrity has been restored.

The final phase of repair is extra-cellular matrix maturation and remodeling. This phase is probably most dynamic, in that there is a constant alteration of the matrix. This involves degradation of fibronectin and a simultaneous increase in production of collagen content. As healing continues, the accumulation of collagen results in a stronger scar and a decrease in scar mass.

As can be appreciated, the process of wound healing is a complex series of biochemical and physiological changes.

For many years, physicians considered the exposure of wounds to the air as essential for healing. However, wounds exposed to air become dry and fall below the surface of the surrounding skin in such a way as to interfere with the proliferation and migration of cells. Recently, occlusive wound care clearly demonstrated the need for covering the wound to retain moisture so as to prevent the delay in wound healing [see J. Surg. Res. 50:442 (1991), and Arc. Dermatol. 120:1329 (1984)].

It is an aspect of the present invention to describe a composition derived from the Aloe plant which, when used as an adjuvant for the occlusive care of wounds, exhibits improved wound-healing capabilities. This composition is a Aloe vera gel-mucilage mixture (a "bandage") which is placed over the open wound either by itself or as an occlusive material over a separate wound healing composition, such as Aloe vera gel or eserin cream, Vaseline, petrolatum. or commercially available antibiotic gels.

This and other aspects of the present invention will become more apparent to the reader with consideration of the following figures, examples and detailed description of the present invention.

Figure 1:
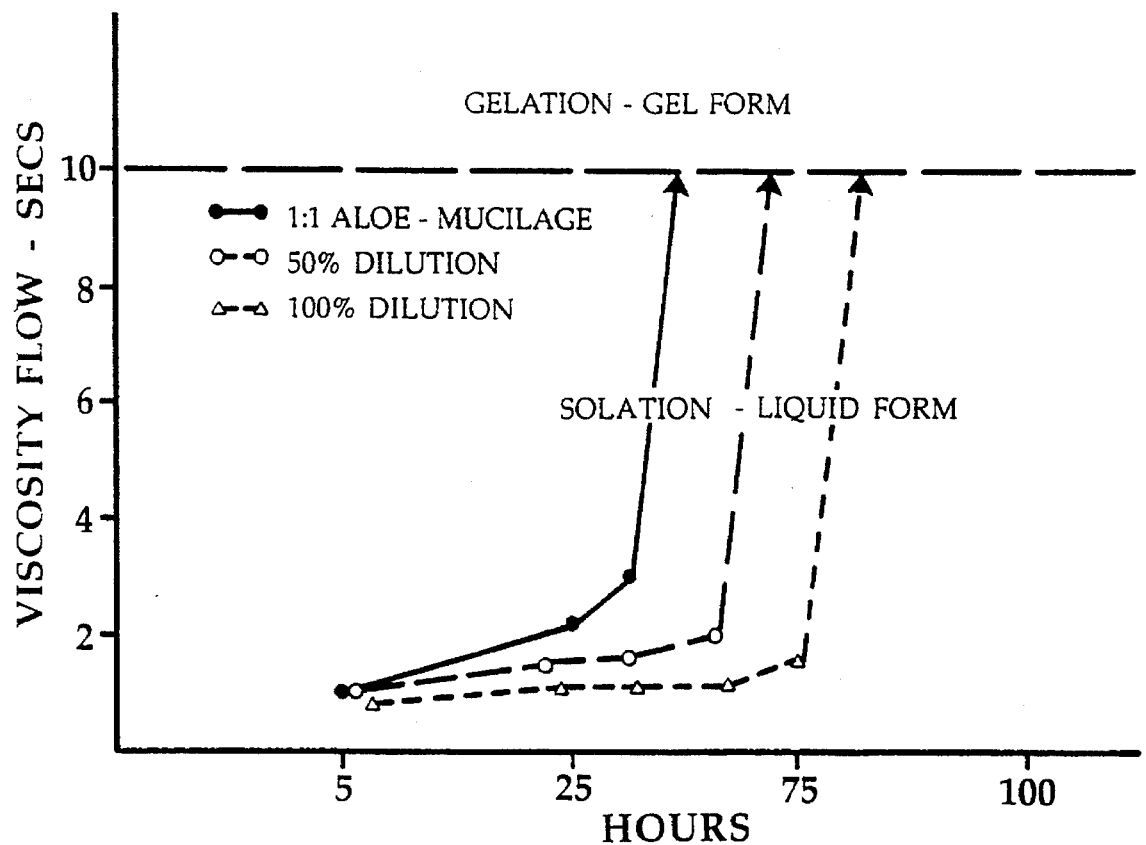
FIG. 1 depicts the effect of dilution on the viscosity of Aloe vera and mucilage in a 1:1 ratio according to the present invention.

Actually a member of the lily family, there are more than 200 species of Aloe, and while many have been used with some success in folk remedies, *Aloe vera barbadensis* has become singularly the most commercially important species for the production of Aloe vera gel (as used hereinafter the gel will be referred to as "Aloe vera" or "gel").

Aloe plants exhibit radial arrangement of 4 rows of leaves alternately arranged. The outer 2 rows are fully developed whereas the inner 2 rows are not fully grown. The inner "pup leaves" receive nourishment from the outer leaves. Low amperage faxitron x-ray observations have noted long "tubes" running from the leaf tip to the base of the leaf which carry nourishment to the young pup leaves.

A cross section of the Aloe leaf reveals an outer epidermis containing guard cells forming stomata through which carbon dioxide enters the green rind. The epidermis is covered with a secreted waxy coat to prevent the escape of water; the rind consists of 15–18 layers of cells interspersed with chloroplasts, and this is the manufacturing portion of the leaf wherein synthesis of carbohydrate, fat and protein takes place. Immediately within the epidermal layer are located vascular bundles consisting of xylem that transports water, minerals and nitrogen from the roots to the green rind, and phloem that transports synthesized materials to other parts of the leaf. These vascular bundles connect with the long tubules seen in the low amperage faxiton X-ray observations running lengthwise toward the leaf base. In addition to these vascular bundles, a third type of tubular structure is found, the large pericyclic tubules that are adherent to the rind and contain the yellow latex or sap that is very high in anthraquinones. Enveloped within the vascular bundle layer of cells lies a "gel fillet" consisting of large and spongy parenchyma cells that store water and large amounts of carbohydrate. Mucilage is a thick and slimy layer of lacunar mesophyll consists of long chain polysaccharide molecules that act as a container enclosing the Aloe vera gel and is located between the rind and the fillet.

When an animal bites the Aloe leaf, the leaf is able to seal the wound within a short period of time so that the Aloe gel fillet does not leak to the outside and to protect the plant from becoming contaminated with a potential phytopathogen. This is quite apparent when the leaf is removed during harvest; at the point of severance, the wound margin physically contracts to prevent gel from escaping. When the cross sectional contraction of the leaf is measured at various distances from the tip, the closer the cuts across the leaf were to the base of the leaf, the greater was the contraction. This response was due to the greater cross sectional area as one moves from tip to base; the amount of mucilage per unit volume of Aloe vera increases to cause a greater sealing of the wound.

Observations made during the research leading to the present invention suggest that mucilage is a long chain mucopolysaccharide. If water is removed from the mucilage, what is left feels and looks like a woven membrane, and these observations provided the incentive to study the use of mucilage in wound healing. What was found was that when mucilage was placed over an open wound, the wound area remained moist and did not drop as seen in dry wounds. As a result, and in accordance with the present invention, when Aloe vera was mixed with exogenous mucilage in approximately a 1:1 ratio (this ratio can vary ±10%, that is 0.9–1.1:0.9–1.1 ratio without any deleterious results to the present invention) the epidermal and fibroblast growth factors found in Aloe vera migrated from the mucilage-Aloe vera "bandage" into the wound to stimulate the host's fibroblasts and epidermal cells for growth and repair. Furthermore host cells would migrate in a proper manner to increase wound healing. The occlusive nature of the mucilage-gel bandage increased wound healing from both mechanical and an endocrine points of view.

Thus, in accordance with our findings, we believed that if the phenomena of wound closure found in the Aloe leaf could be transferred to the human wound, it would provide a major step forward in wound healing and an important therapeutic use for Aloe vera. Our prior research on the movement of water through the skin using gel fillet suggested that Aloe vera gel fillet in high doses would remove water from the skin, a finding that would be undesirable with what is now known and medically desired in the treatment of open wounds. However, if mucilage were mixed with Aloe, as is described by the present invention, we discovered that this does not occur because of the occlusive properties (covering/bandaging) of mucilage. What we discovered was that such a bandage actually increases wound healing from controls without the gel-mucilage bandage. The mucilage-Aloe vera bandage, according to the present invention, re-directs moisture into the skin; in addition, the bandage consisting of the gel-mucilage mixture has been found to possess anti-inflammatory activity.

The Aloe vera gel fillet is a colloidal system in which the particles and the liquid phase can be seen under high power microscopy. The particles appear to be mucopolysaccharide, and the liquid phase consists of water with dissolved materials. In cultivation, the wind normally imparts movement to the leaves, and thereby to the particles of the colloid, converting it to a liquid sol that the plant can move from the leaf tip to the leaf base and on to the "pup leaves" for energy and growth. In short, wind imparts movement to the colloidal particles and makes the Aloe gel more liquid so it can move from the leaf tip to the leaf base. During this process, glucose and gel synthesis within the plant is increased.

Presently there are two commercial processes being used for the production of Aloe vera. The most commonly used method of extracting Aloe vera from the plant is to hand-fillet the Aloe leaf. In this procedure, the leaf is removed from the plant, washed, and the green rind (consisting of the epithelial and chlorophyll-containing layer of cells) is removed by hand leaving the inner fillet. The inner fillet is then washed with water to remove the yellow sap (containing aloin which further contains many undesirable anthraquinones) and mucilage. The fillet is then ground and the pulp (consisting mainly of the cellulose cell wall from the cells within the pulp) is removed, and the resulting Aloe vera is either freeze dried or made into solution.

The second method is the "whole leaf" method by which the whole leaf is removed from the plant, coarsely chopped, and filtered to remove the rind material. The liquid portion containing the fillet and aloin is treated to remove the aloin by activated charcoal.

In both instances, the purpose of Aloe vera preparation is to obtain a clear product that is aloin-free, cellular-free, pulp-free, and mucilage-free.

EXAMPLE 1

Preparation of Aloe vera-mucilage bandage

Aloe vera gel was obtained from commercial sources using the whole leaf process for Aloe vera production. These sources also supplied discarded aloin-free mucilage and discarded Aloe pulp for the studies that went into the making of the present invention. The mucilage was supplied from the process waste stream by the commercial processor without dilution, and was added to Aloe gel in different ratios in accordance with the specific studies being conducted.

The following description of the present invention uses the preparation made in accordance with the process as depicted in Example 1.

Figure 2:
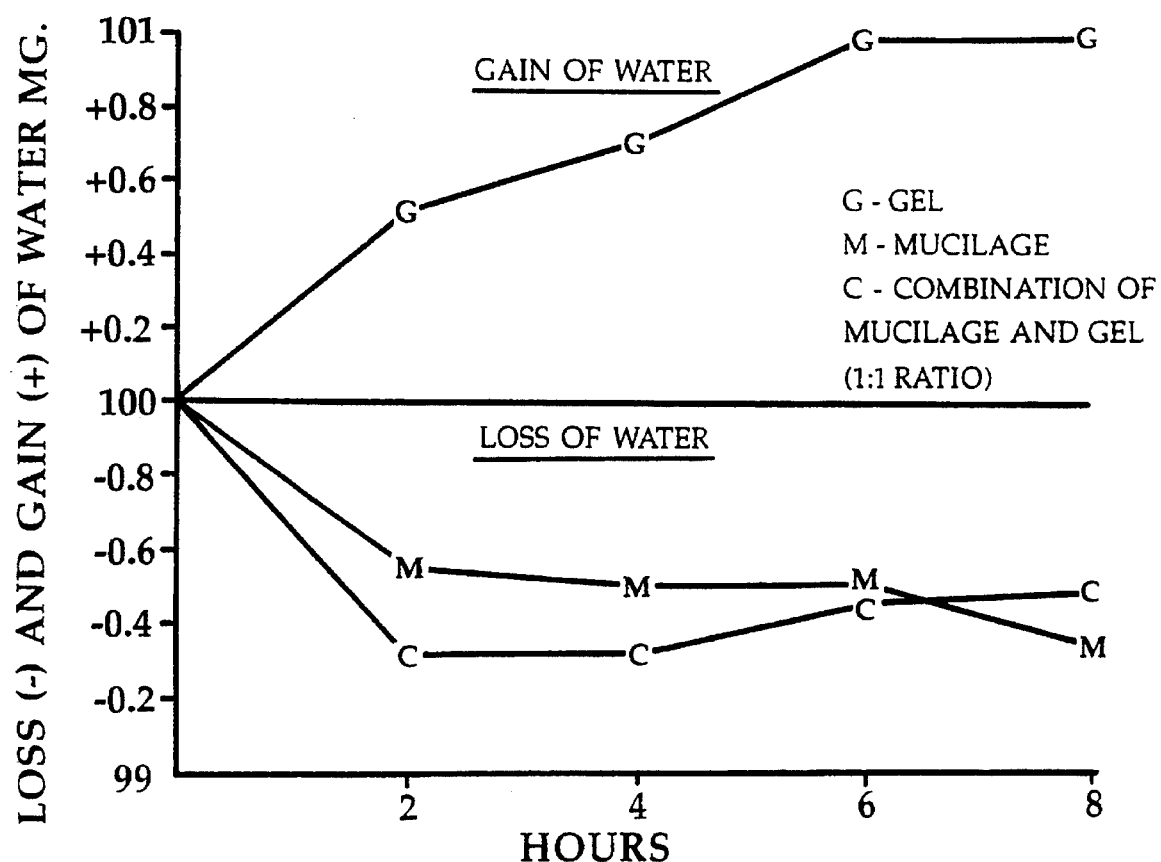
FIG. 2 depicts the effect that mucilage has on preventing the gain of water by aloe vera gel according to the present invention.

The Sol-Gel transformation of dilutions of a 1:1 mixture of dried whole plant Aloe powder and mucilage indicates that dilution of this gel with water reduces the amount of gelation. Normally, Aloe vera is hydroscopic, that is, it quickly picks up water and therefore the use of Aloe vera gel on an open wound is undesirable as it would dry rather than moisturize the wound. However, with the 1:1 Aloe mixture, dilution from 1:1 aloe-mixture to 50% to 100% with water delays the transformation from a sol to a gel (see FIG. 1). This indicates that a 1:1 mixture of Aloe with mucilage causes liquid, mainly water, in the gel to move away from the gel as shown by the decrease in viscosity with time. Thus, moisture is not being absorbed into the Aloe gel by the presence of the exogenous Aloe mucilage. In fact, when the gain and loss of water is compared between the gel, mucilage, and the 1:1 ratio of mucilage and Aloe according to the present invention, only the Aloe gel was found to gain water (see FIG. 2). Both the mucilage and the combination of the Aloe gel and the mucilage (1:1 ratio) lost water. The presence invention has therefore reversed the movement of water away from the Aloe by providing the addition of mucilage.

The advantage of such a bandage of mucilage and Aloe gel is that it allows for the movement of moisture, which contains growth and anti-inflammatory factors capable of being used by the host animal, to the wound.

The occlusive nature of mucilage increases wound healing by both mechanical and endocrine means. By providing epidermal and fibroblast growth factors found within the gel to the wound at the same time it causes the gel to give up water to the wound, the mucilage-Aloe bandage according to the present invention stimulates the wounded host's fibroblast and epidermal cells for enhanced growth and repair of the wound. In addition to stimulating the action of fibroblasts and epidermal cells, the use of the Aloe vera-mucilage bandage according to the present invention is also anti-inflammatory. The bandage (i.e. the combination of Aloe vera gel and mucilage) reduces inflammation as measured by a decrease in mast cells, Polymorphonuclear leukocytes and vascularity.

The croton oil-induced ear swelling assay is used conventionally in pharmacology to determine the anti-inflammatory ability of compounds. In view of its acceptance in the research community, this assay was also used to determine the anti-inflammatory abilities of the present invention according to the following example:

EXAMPLE 2

Anti-inflammatory assay

Adult male ICR mice (40 to 50 g; 10–12 animals per group) were given 10 µl of 25 µg/µl croton oil in acetone (acetone alone produces no effect when applied topically to the ear) applied topically to the inner surface of the right ear of each mouse. The left ear served as an untreated control. The croton oil is normally applied using a microsyringe. A peak swelling occurred 6 hours following application, at which time the right (inflamed) and left (control) ears were biopsied with a 6 mm punch, and the ear tissue weighed to the nearest 0.1 mg. The difference between the right and left ears represent the degree of swelling. In determining the effect of Aloe vera according to the present invention, a 1% or 5% dosage of Aloe vera was applied to both ears 30 minutes following application of the croton oil. This provided a 3.8% or 33.7%, respectively, potential anti-inflammatory response.

The results from this example indicated a dose-response relationship on topical croton oil induced edema with mucilage. A 1% dose decreased edema 3.8%, whereas a 5% dose of mucilage inhibited inflammation 33.7%.

The tensile strength of the Aloe gel-mucilage bandage (in a 1:1 ratio according to the present invention) is 1228.2±30 gms. In other words, when used as an adhesive, it took this amount of force to break the bond formed utilizing a 1:1 ratio of Aloe gel-mucilage as an adhesive. When the environmental temperature surrounding the adhesive (i.e. the 1:1 Aloe-mucilage) was increased, the gel initially applied at 23° C. did not release until it was transformed into a sol phase at 54° C. As this temperature could never be reached in the living human body (which is conventionally at approximately 37° C.) the 1:1 ratio Aloe-mucilage gel according to the present invention also may be used as a bone adhesive until such time as ossification between two bone segments takes place; and during this time the various growth factors reported by others to be present in Aloe gel would also be available to stimulate and enhance the body's repair mechanism.

The wound healing effect of the 1:1 mixture of mucilage-Aloe vera gel according to the present invention was also studied. In these experiments, two parallel wounds were opened on the backs of mice; the "test" wound received a 1:1 mixture (bandage) of mucilage-Aloe vera gel for 3 days while the "control" wound was left untreated. The percentage of reduction of the wound for the untreated control over this period of time was 11%, while the percentage of reduction of the wound treated with the Aloe gel-mucilage bandage was 46%, a 4-fold improvement in wound healing. This was apparently due to both the occlusive and endocrine properties of the 1:1 gel bandage.

Figure 3:
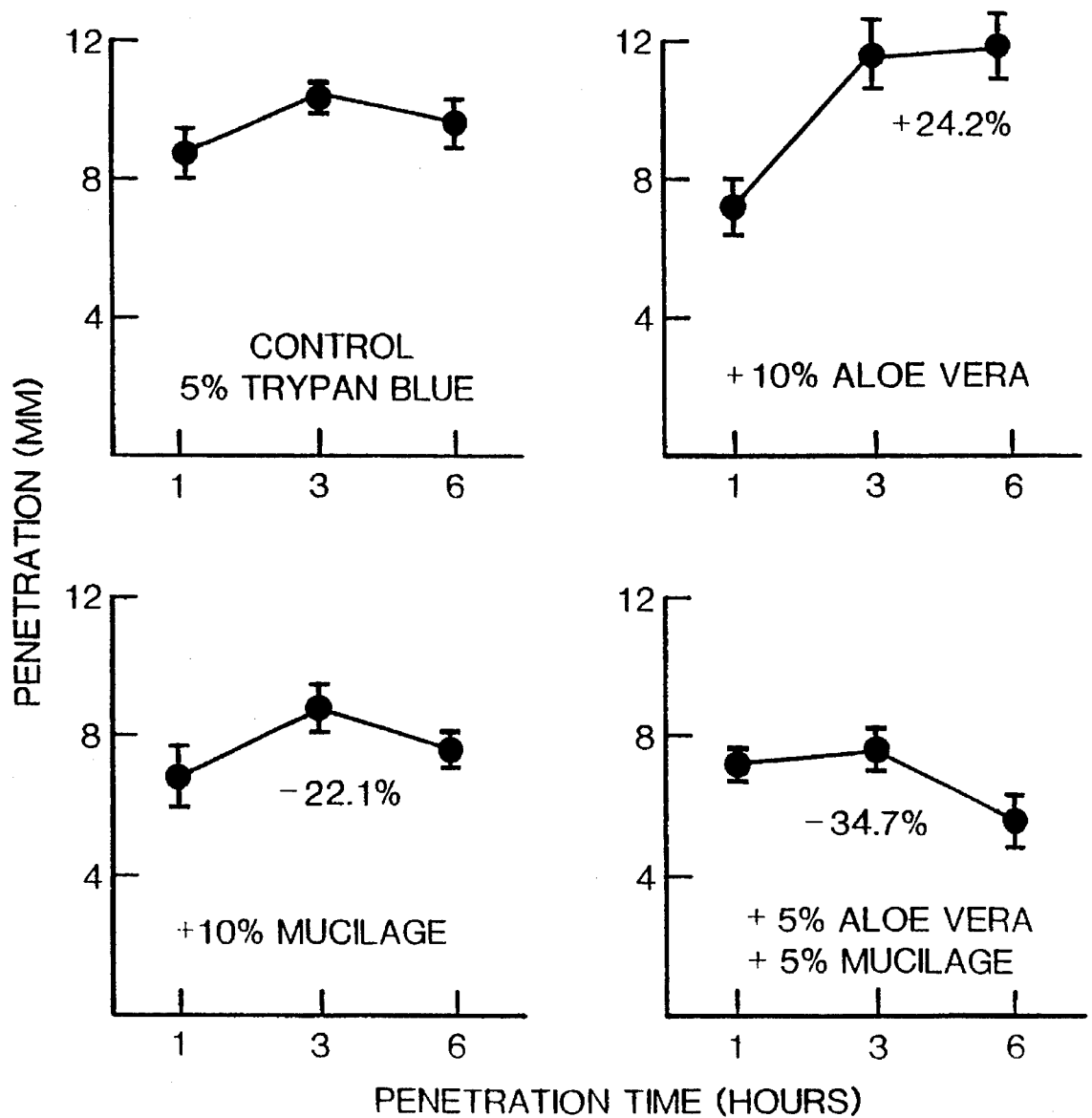
FIG. 3 depicts the influence of mucilage and Aloe vera on skin penetration (in mm) of 5% trypan blue over six hours.

The influence of mucilage and Aloe vera on skin penetration (in mm) of a bandage according to the present invention can be seen in FIG. 3.

EXAMPLE 3

Trypan blue penetration assay

A small amount (less than 0.1 ml) of 5% trypan blue in saline (to serve as a control) was injected just under the skin of a mouse, and an initial measurement of the diameter of the resulting colored area was taken. Measurements were also taken over a period of time to determine the rate at which the trypan blue penetrated the surrounding tissue. In addition, solutions containing 5% trypan blue in the presence of varying concentrations of Aloe vera, Aloe vera plus mucilage, and mucilage alone were injected under the skin of mice and the diameter of the resulting colored area was taken initially and over a period of time.

As noted and described in FIG. 3, the 5% Aloe vera-5% mucilage bandage according to the present invention blocks the penetration of trypan blue through the skin whereas Aloe vera alone increases trypan blue penetration through the skin. Thus, If one places Aloe vera gel on the wound, and over this initial application secondly places a 1:1 mucilage-Aloe vera mixture (that is the bandage according to the present invention, one has the ideal "wound healer".

In order to determine the effect of the approximately 1:1 ratio of Aloe vera-mucilage according to the present invention, we devised a method of measuring the strength of wounds by estimating the point at which the integrity of the wound is broken by the distention of air.

Figure 4:
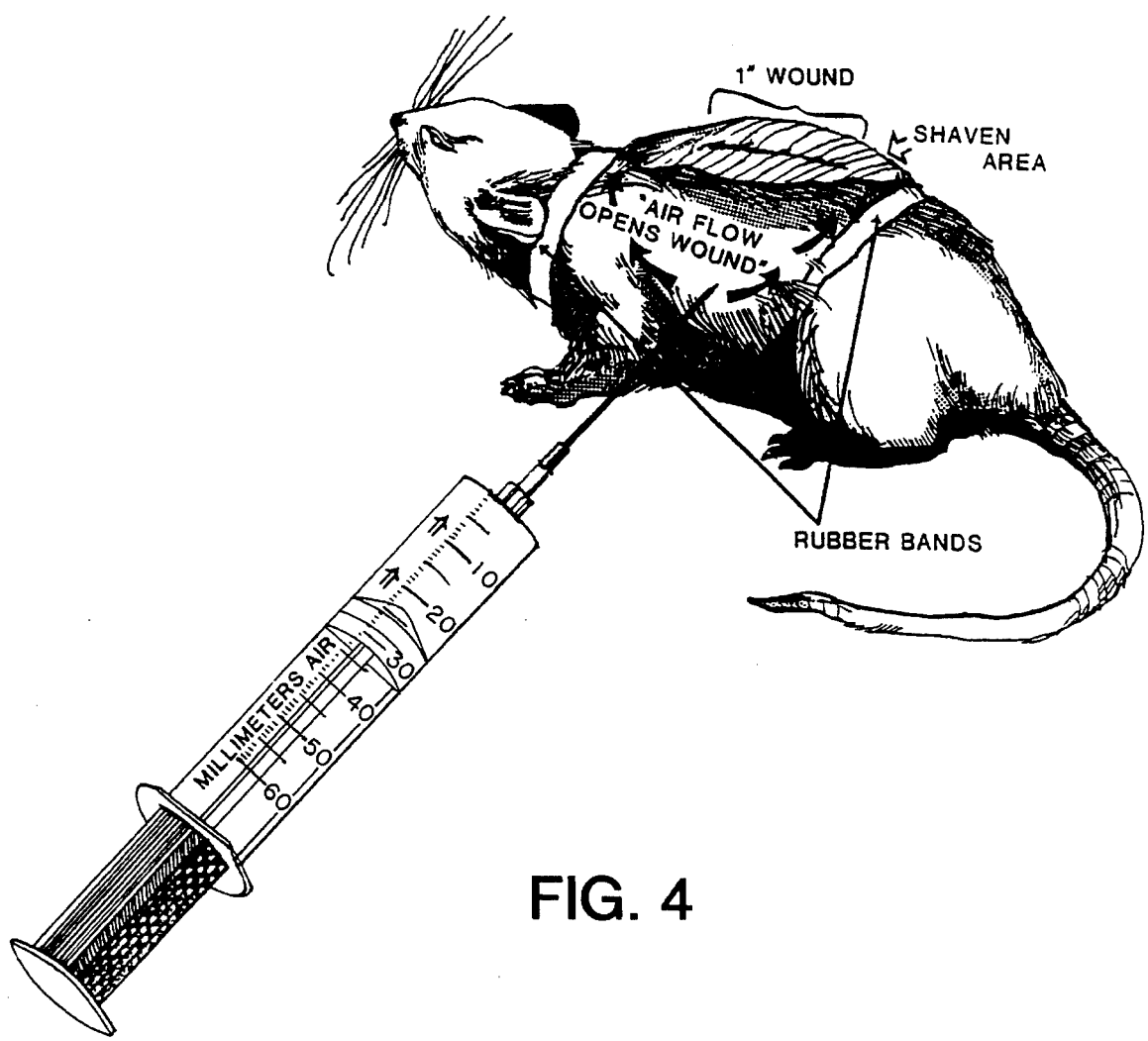
FIG. 4 depicts the method by which the tensile strength assay as described herein was conducted.

As seen in FIG. 4, the back of a mouse is shaven of all hair and a one inch incision is made through the epidermis along the spine. While tensile strength of wounds is measured in terms of the load applied per unit of cross section area, the breaking strength is the measure of force required to break a wound of tissue without regard to dimensions. While tensile strength is not a function of the incision length, breaking strength is. The measurements of force required to pull a wound apart differ chiefly in the manner in which the force is applied and the sophistication of the force measurement. In the data recorded herein and in the data collected in the making of the present invention, we used a conventional plastic syringe calibrated to measure mm of air injected into the peritoneal cavity of the mouse. In the tensile strength assay, the wound is allowed to heal for a set period of time (normally 3–5 days) at which time the peritoneal cavity is filled with air (at a rate of injection of 1 mm of air per second) using the syringe as depicted in FIG. 4. Elastic bands are first placed on over the shoulders and hips of the animal to contain the injected air into a defined area of the body and to reduce error involving underlying tissue of the peritoneal cavity, and air is injected into the animal until the wound is disrupted at which time the volume of air is recorded. This relatively simple procedure was very sensitive and accurate for measuring tensile strength of wounds.

Figure 5:
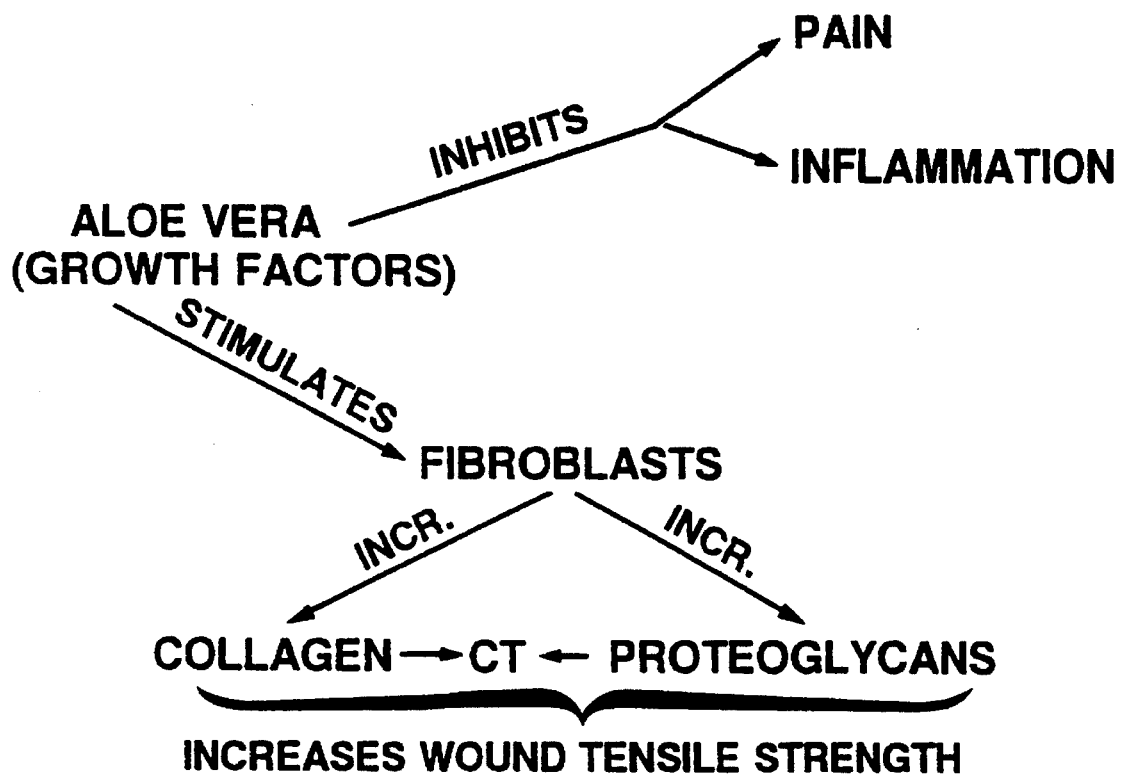
FIG. 5 depicts the mechanism of action of Aloe vera for increasing the wound tensile strength in the Aloe vera-mucilage bandage according to the present invention.

As shown in FIG. 5, the mechanism of action of Aloe vera gel when used in accordance with the bandage according to the present invention is believed to occur because growth factors in the gel Aloe vera inhibits both pain and inflammation while stimulating the number of fibroblasts to increase the formation of collagen and proteoglycans.

In experiments conducted during the research leading to the present inventions—the use of about a 1:1 mixture of Aloe vera and mucilage in wound healing—an unexpected synergistic effect was found with the use of whole plant Aloe mucilage. When increases in wound tensile strength were compared using four different test compositions as bandages for wounds in mice, it was found that the use of whole plant Aloe mucilage greatly increased the tensile strength in 1:1 Aloe vera-mucilage bandages. This is reported in the following table which indicates the effect of whole plant Aloe mucilage (at a 1:1 ratio of Aloe gel to mucilage) at 1 and 5% doses in petrolatum over four days with 0.5% added Aloe "pulp" (cellulose obtained from the cell wall material taken from the cells contained in the fillet during processing; this is an undesirable end-product that is discarded in the preparation of Aloe vera gel).

TABLE 1

| Bandage Composition | Increase In Tensile Strength |
| --- | --- |
| Aqueous Control | 0% |
| Petrolatum Control | 30% |
| 1% Aloe in Petrolatum | 18% |
| 5% Aloe in Petrolatum | 60% |
| 5% Aloe in Petrolatum + 0.5% Aloe pulp | 131% |

As tabulated, the 1% Aloe and mucilage increased the tensile strength of the wound 18%. However, increasing the dose of the combination to 5% produced a 60% increase in tensile strength over controls. Adding 0.5 Aloe pulp to the 5% Aloe and mucilage increased the wound tensile strength still further to 131%. a dose-response relationship is evident with a further increase in response by adding the Aloe pulp. The mucilage with its growth factors and tightly woven mucopolysaccharide chains combined with Aloe to form a strong gel in which the polysaccharide fibers bond together to increase tensile strength. Adding the Aloe pulp caused these fibers to form a network with the 1:1 gel which gave the strongest preparation thus far seen with Aloe vera. As the wound heals, the bandage according to the present invention, whether it is the use of an Aloe-mucilage bandage per se, the use of the bandage over a separate wound healing composition such as Aloe vera gel, or the use of an Aloe-mucilage bandage with added Aloe pulp, will become integral with the formation of the scab and will be sloughed-off with the scab.

Accordingly, the present invention describes the sealing effect of Aloe vera gel and mucilage to an animal wound. In addition, by the addition of the additional component of fibers obtained from aloe pulp, In addition to the use of an Aloe vera gel-mucilage bandage according to the present invention, additional tests were conducted to determine if the combination of Aloe and aspirin given topically might have an effect on the inhibition of croton oil induced ear swelling in an attempt to determine whether the addition of water soluble compounds might be placed in an Aloe vera-mucilage bandage (either in the bandage or in a composition such as Aloe vera gel plus aspirin initially placed on the skin and covered with the bandage) according to the present invention and be carried through the epidermal barrier to the blood vessels in the dermis.

EXAMPLE 4

Anti-inflammatory assay

Four groups (10 mice per group) of adult male ICR-HSD mice was given topically 25 µg/per 10 µl croton oil solutions. This irritant was applied to the inner surface of the animal's right ear, and the left ear was not treated and used as a control. One-half hour after the application of the croton oil irritant, solutions were added topically to reduce inflammation; the solutions were 1% aspirin, 2% Aloe and a solution that had both aspirin and aloe.

Six hours after the topical application of croton oil solutions, a 6 mm biopsy punch specimen was taken from each ear, weighed, and the weight differences between the two were compared to determine the amount of inflammation remaining on the right ear.

We found that aspirin (micronized aspirin) added to Aloe vera gave an additive effect on the inhibition of croton oil-induced ear swelling in mice (9 per group) as depicted in the following table:

TABLE 2

| Treatment (µg) | Inhibition (%) |
| --- | --- |
| Aloe (200) | 18.7 ± 1.6 |
| Aspirin (100) | 23.7 ± 3.1 |
| Aloe (200) + Aspirin (100) | 42.4 ± 3.0 |

Thus, it is clear from the data collected that aspirin, preferably micronized aspirin as this is more soluble than conventional commercial grade aspirin, may be topically administered to the skin of an animal host by admixing the aspirin with aloe vera according to the present invention. In addition, should one want to "push" the analgesic into the tissues, the topical application may be covered with the Aloe vera-mucilage bandage according to the present invention which, as indicated above, because of its occlusive nature will cause the solubilized materials in the Aloe vera to be directed into the tissues. Although 200 µg of aspirin was used in obtaining the tabulated data, the actual amount of aspirin that may be used for the intended analgesic purpose will, of course, be determined by the degree of analgesia desired and may vary from "child" to "adult" dosages. What will determine the amount of analgesic to be added to the Aloe gel vehicle will be the amount sufficient to bring about the desired effect.

Another of our interests is with the use of gibberellin as a potential for wound healing, and as part of the present invention we studied the effect of adding gibberellin to the Aloe vera used in conjunction with the examples reported herein. Gibberellin is a plant-derived growth factor present in Aloe vera which plays a major role in the plant's growth and development, but to our knowledge, no one has previously shown that this plant growth factor has anti-inflammatory and wound healing therapeutic potential in animals. Gibberellins are one of five major types of plant growth factors which have been identified. Gibberellin was first shown to be produced by a rice fungus by a Japanese plant pathologist who isolated the gibberellin and showed that it was involved in growth and development of plants such as sugar cane, barley, wheat, rice and maize. Gibberellin is conventionally purified by being absorbed onto charcoal and then being eluted off by acetone, alcohol or ether. Since the procedure for preparing Aloe vera involves the decolorization of the gel with charcoal, we believed that it was possible that the decolorizing step in the manufacture of Aloe vera also removed gibberellins, and that if these were returned to the gel, that it might act as a growth factor for animal tissues as well as for the reported use of this material in stimulating plant growth. We therefore set out to investigate the effect of gibberellin on open wounds.

EXAMPLE 5

Open wound healing assay:

Adult male ICR mice (30 g, 15 animals/group) were anesthetized with ether and shaved on both sides of the back. A sterile 6 mm Baker biopsy punch was used to induce a wound on each side of the vertebral column. Anterior-posterior wound diameter measurements were made using a vernier caliper on days 0, 4 and 7. Three treatment groups received daily subcutaneous injections of a gibberellic acid ($GA_3$) solution at dosages of 2, 10 and 100 mg/Kg, respectively. Control mice received daily injections of saline on a 10 ml/Kg basis. Standard errors for each mean value was calculated. The student's "t" test was used to determine significant differences between treatment and control groups. An analysis of variance (ANOVA) was also calculated to determine the statistical significance of the study as a whole, and gave a Fisher ratio at 16.48 which is significant at $p<0.001$.

EXAMPLE 6

Wound tensile strength assay

Adult male Sprague Dawley mice (30 g, 10 animals/group) had a 1-inch surgical incision placed on their shaven back under ether anesthesia. Each wound was closed with a 9 mm wound clip at 0.25-inch spacings for a total of 3 clips per wound. Mice were daily subcutaneously injected for 4 days beginning on the day of surgery with 50 mg/Kg of whole leaf Aloe vera or with 50 mg/Kg gibberellin or with the combination of the two (50 mg/Kg of whole leaf Aloe vera and 50 mg/Kg gibberellin). Six hours after the day 4 injection, the tensile strength of wounds was measured by injecting air into the peritoneal cavity from a syringe as described above.

The results for the effect of gibberellin on wound healing in mice described above are tabulated below:

TABLE 3

| composition | decrease (%) in wound diameter |
|---|---|
| Saline control | 60.0 ± 8.3 |
| Gibberellin 2 mg/kg | 65.3 ± 11.3 |
| Gibberellin 10 mg/kg | 71.6 ± 12.1 |
| Gibberellin 100 mg/kg | 81.7 ± 7.0 |

Thus, it is apparent that gibberellin brought about wound healing when administered to animals.

The wound tensile strength of whole leaf Aloe vera subcutaneously administered as a vehicle for gibberellin showed a clear cut additive response as depicted in the following table:

TABLE 4

| composition | increase (%) in wound tensile strength |
|---|---|
| Aloe 50 mg/kg × 4 | 14.8 ± 0.6 |
| Gibberellin 50 mg/kg × 4 | 36.1 ± 1.5 |

TABLE 4-continued

| composition | increase (%) in wound tensile strength |
|---|---|
| Aloe + Gibberellin (50 mg/kg each × 4) | 49.7 |

Thus, not only does this indicate that Aloe vera is a good vehicle for gibberellin, but that the biological activities of each component could be added together when administered together. Thus, gibberellin may also be administered in the wound-healing bandage according to the present invention for providing added tensile strength, and added wound healing, for the treatment of open wounds.

Thus while I have illustrated and described the preferred embodiment of my invention, it is to be understood that this invention is capable of variation and modification and I therefore do not wish to be limited to the precise terms set forth, but desire to avail myself of such changes and alterations which may be made for adapting the invention to various usages and conditions. Accordingly, such changes and alterations are properly intended to be within the full range of equivalents, and therefore within the purview of the following claims.

Having thus described my invention and the manner and process of making and using it in such full, clear, concise, and exact terms so as to enable any person skilled in the art to which it pertains, or with it is most nearly connected, to make and use the same,

I claim:

1. A method for the therapeutic treatment of open wounds in animals that comprises: (1) adding a first wound-healing composition to an open wound, and (2) overlaying the first wound-healing composition with a bandaging mixture comprising about a 1:1 ratio of whole leaf Aloe vera and Aloe vera mucilage.

2. A method according to claim 1 wherein the first open wound-healing composition comprises Aloe vera and gibberellin.

3. A composition for use as an occlusive adjuvant in the treatment of animal wounds which comprises a mixture of Aloe vera and Aloe vera mucilage in a ratio of about 1:1.

4. A composition for the therapeutic treatment of an animal which consists of a therapeutic composition of Aloe vera and an active component selected from the group consisting of micronized aspirin and gibberellin.

5. The composition according to claim 4 wherein the active component is micronized aspirin.

6. The composition according to claim 4 wherein the active component is gibberellin.

7. A composition for the therapeutic treatment of an animal which consists of Aloe vera and gibberellin.

8. A composition according to claim 7 wherein the amount of gibberellin in said composition is between 2 and 100 mg/kg based upon the weight of the animal to receive said composition.

* * * * *